(12) United States Patent  (10) Patent No.: US 8,535,273 B2
Vaillancourt et al.  (45) Date of Patent: Sep. 17, 2013

(54) DEVICE FOR REMOVING A HUBER NEEDLE FROM A PATIENT

(75) Inventors: Michael J. Vaillancourt, Chester, NJ (US); Marshall Kerr, Carlsbad, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 13/546,891

(22) Filed: Jul. 11, 2012

(65) Prior Publication Data

US 2012/0277691 A1   Nov. 1, 2012

Related U.S. Application Data

(63) Continuation of application No. 12/316,475, filed on Dec. 11, 2008, now Pat. No. 8,231,582.

(51) Int. Cl.
*A61M 5/32*       (2006.01)

(52) U.S. Cl.
USPC ................. 604/177; 604/174; 604/164.04

(58) Field of Classification Search
USPC ............ 604/272–274, 96.01, 164.01–170.03, 604/523
See application file for complete search history.

(56) References Cited

U.S. PATENT DOCUMENTS

| | | |
|---|---|---|
| 2,847,995 A | 8/1958 | Adams |
| 2,876,770 A | 3/1959 | White |
| 2,925,083 A | 2/1960 | Craig |
| 3,134,380 A | 5/1964 | Armao |
| 3,306,290 A | 2/1967 | Weltman |
| 4,160,450 A | 7/1979 | Doherty |
| 4,564,054 A | 1/1986 | Gustavsson |
| 4,592,744 A | 6/1986 | Jagger et al. |
| 4,631,058 A | 12/1986 | Raines |
| 4,632,671 A | 12/1986 | Dalton |
| 4,645,494 A | 2/1987 | Lee et al. |
| 4,645,495 A | 2/1987 | Vaillancourt |
| 4,725,267 A | 2/1988 | Vaillancourt |
| 4,760,847 A | 8/1988 | Vaillancourt |
| 4,813,939 A | 3/1989 | Marcus |
| 4,846,809 A | 7/1989 | Sims |
| 5,013,305 A | 5/1991 | Opie et al. |
| 5,053,017 A | 10/1991 | Chamuel |
| 5,092,852 A | 3/1992 | Poling |
| 5,176,655 A | 1/1993 | McCormick et al. |

(Continued)

FOREIGN PATENT DOCUMENTS

| | | |
|---|---|---|
| DE | 3808688 A1 | 1/1989 |
| DE | 3802353 A1 | 8/1989 |

(Continued)

OTHER PUBLICATIONS

U.S. Appl. No. 12/316,475, filed Dec. 11, 2008 Final Office Action dated Dec. 30, 2009.

(Continued)

*Primary Examiner* — Kevin C Sirmons
*Assistant Examiner* — Brandy S Lee
(74) *Attorney, Agent, or Firm* — Rutan & Tucker, LLP

(57) ABSTRACT

A one-piece connector for removing a housing and needle of a Huber needle assembly from a patient. The connector has a frame that can be positioned about a surface on the housing of the needle assembly and a pair of wings that pivot toward one another to provide a gripping surface.

8 Claims, 2 Drawing Sheets

(56) References Cited

U.S. PATENT DOCUMENTS

| | | |
|---|---|---|
| 5,295,972 A | 3/1994 | Mischenko |
| 5,312,371 A | 5/1994 | Dombrowski et al. |
| 5,334,158 A | 8/1994 | McLees |
| 5,336,187 A | 8/1994 | Terry et al. |
| 5,419,766 A | 5/1995 | Chang et al. |
| 5,487,728 A | 1/1996 | Vaillancourt |
| 5,487,733 A | 1/1996 | Caizza et al. |
| 5,490,841 A | 2/1996 | Landis |
| 5,498,241 A | 3/1996 | Fabozzi |
| 5,531,713 A | 7/1996 | Mastronardi et al. |
| 5,575,773 A | 11/1996 | Song et al. |
| 5,584,818 A | 12/1996 | Morrison |
| 5,685,860 A | 11/1997 | Chang et al. |
| 5,695,474 A | 12/1997 | Daugherty |
| 5,779,679 A | 7/1998 | Shaw |
| 5,817,070 A | 10/1998 | Tamaro |
| 5,853,393 A | 12/1998 | Bogert |
| 5,858,004 A | 1/1999 | Shields |
| 5,885,255 A | 3/1999 | Jaeger, Jr. et al. |
| 6,042,570 A | 3/2000 | Bell et al. |
| 6,238,375 B1 | 5/2001 | Powell |
| 6,497,669 B1 | 12/2002 | Kensey |
| 6,500,155 B2 | 12/2002 | Sasso |
| 6,623,462 B2 | 9/2003 | Guzzo et al. |
| 6,629,959 B2 | 10/2003 | Kuracina et al. |
| 6,659,984 B2 | 12/2003 | Maclean Crawford et al. |
| 6,689,102 B2 | 2/2004 | Greene |
| 6,699,217 B2 | 3/2004 | Bennett et al. |
| 6,719,727 B2 | 4/2004 | Brimhall et al. |
| 6,749,588 B1 | 6/2004 | Howell et al. |
| 6,808,509 B1 | 10/2004 | Davey |
| 6,824,530 B2 | 11/2004 | Wagner et al. |
| 6,926,693 B2 * | 8/2005 | Enns .................. 604/165.03 |
| 6,932,803 B2 | 8/2005 | Newby |
| 6,969,372 B1 | 11/2005 | Halseth |
| 6,972,002 B2 | 12/2005 | Thorne |
| 7,147,623 B2 | 12/2006 | Mathiasen |
| 7,150,725 B2 | 12/2006 | Wilkinson |
| 7,214,208 B2 | 5/2007 | Vaillancourt et al. |
| 7,361,159 B2 | 4/2008 | Fiser et al. |
| 7,407,493 B2 | 8/2008 | Cane' |
| 7,438,703 B2 | 10/2008 | Barrus et al. |
| 7,601,139 B2 | 10/2009 | Woehr et al. |
| 7,604,616 B2 | 10/2009 | Thoresen et al. |
| 7,637,893 B2 | 12/2009 | Christensen et al. |
| 7,717,888 B2 | 5/2010 | Vaillancourt et al. |
| 7,776,016 B1 | 8/2010 | Halseth et al. |
| 8,066,678 B2 | 11/2011 | Vaillancourt et al. |
| 2001/0039401 A1 | 11/2001 | Ferguson et al. |
| 2002/0055711 A1 | 5/2002 | Lavi et al. |
| 2002/0099340 A1 | 7/2002 | Crawford et al. |
| 2002/0151852 A1 | 10/2002 | Crawford et al. |
| 2002/0165497 A1 | 11/2002 | Greene |
| 2002/0177816 A1 | 11/2002 | Brimhall et al. |
| 2002/0183652 A1 | 12/2002 | Kensey |
| 2003/0093101 A1 | 5/2003 | O'Heeron et al. |
| 2003/0105430 A1 | 6/2003 | Lavi et al. |
| 2003/0114797 A1 | 6/2003 | Vaillancourt et al. |
| 2003/0144627 A1 | 7/2003 | Woehr et al. |
| 2003/0181872 A1 | 9/2003 | Newby |
| 2003/0199827 A1 | 10/2003 | Thorne |
| 2004/0044318 A1 | 3/2004 | Fiser et al. |
| 2004/0049159 A1 | 3/2004 | Barrus et al. |
| 2004/0236288 A1 | 11/2004 | Howell et al. |
| 2005/0027263 A1 | 2/2005 | Woehr et al. |
| 2005/0090784 A1 | 4/2005 | Nielsen et al. |
| 2005/0107743 A1 | 5/2005 | Fangrow |
| 2005/0107749 A1 * | 5/2005 | Smith et al. .................. 604/263 |
| 2005/0124938 A1 | 6/2005 | Yang |
| 2005/0137528 A1 | 6/2005 | Wilkinson |
| 2006/0135910 A1 | 6/2006 | Luther et al. |
| 2006/0155245 A1 | 7/2006 | Woehr |
| 2006/0161116 A1 | 7/2006 | Willis et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0073221 A1 | 3/2007 | Bialecki et al. |
| 2007/0073222 A1 | 3/2007 | Lilley et al. |
| 2008/0147003 A1 | 6/2008 | Menzi et al. |
| 2008/0177234 A1 | 7/2008 | Keaton et al. |
| 2008/0262434 A1 | 10/2008 | Vaillancourt |
| 2009/0005743 A1 | 1/2009 | Vaillancourt et al. |
| 2009/0254050 A1 | 10/2009 | Bottcher |
| 2009/0281499 A1 | 11/2009 | Harding et al. |
| 2010/0152677 A1 | 6/2010 | Vaillancourt et al. |

FOREIGN PATENT DOCUMENTS

| | | |
|---|---|---|
| DE | 20210394 U1 | 9/2002 |
| EP | 451040 A1 | 10/1991 |
| EP | 0747082 A2 | 12/1996 |
| EP | 0763369 A1 | 3/1997 |
| EP | 1430921 A2 | 6/2004 |
| FR | 2684006 A1 | 5/1993 |
| JP | 61-25558 A | 5/1994 |
| JP | 6226919 A | 8/1994 |
| JP | 7-148270 A | 6/1995 |
| JP | 9099071 A | 4/1997 |
| JP | 2002345955 A | 12/2002 |
| JP | 4355567 | 8/2009 |
| WO | 9400172 A1 | 1/1994 |
| WO | 9806642 | 2/1998 |

OTHER PUBLICATIONS

U.S. Appl. No. 12/316,475, filed Dec. 11, 2008 Final Office Action dated Jan. 25, 2011.

U.S. Appl. No. 12/316,475, filed Dec. 11, 2008 Non-Final Office Action dated Aug. 25, 2010.

U.S. Appl. No. 12/316,475, filed Dec. 11, 2008 Non-Final Office Action dated Mar. 18, 2010.

U.S. Appl. No. 12/316,475, filed Dec. 11, 2008 Non-Final Office Action dated May 29, 2009.

U.S. Appl. No. 12/316,475, filed Dec. 11, 2008 Non-Final Office Action dated Sep. 29, 2011.

U.S. Appl. No. 12/316,475, filed Dec. 11, 2008 Non-Final Office Action dated Sep. 4, 2009.

* cited by examiner

DEVICE FOR REMOVING A HUBER NEEDLE FROM A PATIENT

This application is a continuation of U.S. patent application Ser. No. 12/316,475, filed Dec. 11, 2008, now U.S. Pat. No. 8,231,582, which is incorporated by reference in its entirety into this application.

This invention relates to a device for removing a Huber needle from a patient.

Needle protectors are well known and have been in use for many years with needles used with hypodermic syringes. Conventionally, needles are made with hubs and sockets adapted to be attached to the reduced end of a syringe. A molded plastic cap is conventionally removably secured to the hub of the needle. After mounting the needle on the syringe, the cap is removed to expose the needle for use.

Accidental needle stick injuries, unfortunately, are still common in health care workers, such as nurses, physicians, laboratory workers and housekeeping personnel. Needle stick exposures can result in transmission of hepatitis B, as well as acquired immune deficiency syndrome—AIDs, or other transmittable diseases. The health hazards associated with needle stick injuries are of greater risk for health care workers now than ever before.

Accidental needle sticks often occur when a blood drawer attempts to recap a needle after use or leaves a contaminated needle exposed on work surfaces where the blood drawer or other workers accidentally impale themselves.

As is known, a Huber needle assembly is one that has an L-shaped needle generally mounted with a first leg secured in a housing and a second leg extending from the housing perpendicularly of first leg. In some cases, such as described in U.S. patent application Ser. No. 11/788,542 filed Apr. 20, 2007, published as US 2008/0262434, a cap with a bore for the needle is disposed over the second leg of the needle and is movable from a first position with the needle extending therethrough to a second position with an end of the needle disposed therein in sealed relation. In addition, a tubular sheath is concentrically disposed about the needle in a collapsed state and is secured to and between the housing and the cap. The sheath is extendable from the collapsed state to an extended state in response to movement of the cap from the first position to the second position thereof.

When the Huber needle assembly is being removed from a patient, the cap is held against the skin of the patient while the housing is pulled upwardly to withdraw the needle. During this time, the sheath is extended from its collapsed state to its extended state thereby encasing the needle to prevent an unwanted exposure of the needle or an inadvertent stick. As is known, the cap and housing of the assembly have been provided with wings that facilitate the removal of the needle from a patient.

Accordingly, it is an object of the invention to provide a device that can be readily attached to a Huber needle assembly when in place for removing the assembly from a patient.

It is another object of the invention to provide a relatively simple device that can be attached to a Huber needle assembly for removing the assembly from a patient.

Briefly, the invention provides a connector for connecting to a needle assembly as described in US 2008/0262434 to facilitate removal of a needle from a patient.

The connector is particularly adapted for a Huber needle assembly having a housing with a gripping surface formed, for example, by a pair of parallel upstanding longitudinally extending walls and a flange extending laterally across the top of the walls to form an overhang over each wall. The needle assembly also has one leg of a Huber needle mounted in the housing and a depending leg extending from the housing. A cap is disposed over the depending needle leg with a bore for passage of the leg. The cap is movable relative to the housing from a first position with the needle leg extending therethrough to a second position with an end of the needle disposed therein. A protective sheath is secured between and to the housing and cap to maintain the depending leg in a sealed condition when the cap and housing are moved apart from each other.

The connector has an apertured skeletal frame defining an opening to fit around and under the gripping surface on the housing of the needle assembly. For example, the frame is of rectangular shape for fitting about the walls and under the flange of the needle assembly. The frame is sized so as to be snapped over the flange on the housing of the needle assembly when a Huber needle is being assembled and is not removable once snapped into place.

The connector also has a projection extending from the frame into the rectangular opening of the connector to fit between the walls and under the flange of the housing of the Huber needle assembly. This projection stabilizes the connector and locks the front end of the connector in place against any movement.

In order to facilitate lifting of the frame when the Huber needle assembly is to be removed from a patient, a pair of wings is hinged to opposite sides of the frame for pivoting into contact with each other thereby forming a finger grip that can be grasped by the thumb and index finger of a user. In order to facilitate gripping, each said wing is of trapezoidal shape with a trapezoidal aperture thereby imparting a skeletal construction. In addition, one of the wings has a recess at an end thereof and the other wing has a projection at an end thereof for fitting into the recess of the first wing.

In order to facilitate gripping of the wings when pivoted into contact with each other, the underside of each wing is provided with a rib at the free end. Thus, when the wings are pivoted into contact, the ribs extend outwardly of the wings to provide gripping ledges for the user against which the user can exert a pulling force to remove the Huber needle from a patient.

The frame may be made of any suitable material, such as a semi-rigid polypropylene, that is softer than the housing of the Huber needle assembly. Preferably, the entire connector is made as a one-piece body of plastic.

These and other advantages will become more apparent from the following description taken in conjunction with the accompanying drawings wherein.

Figure 1:
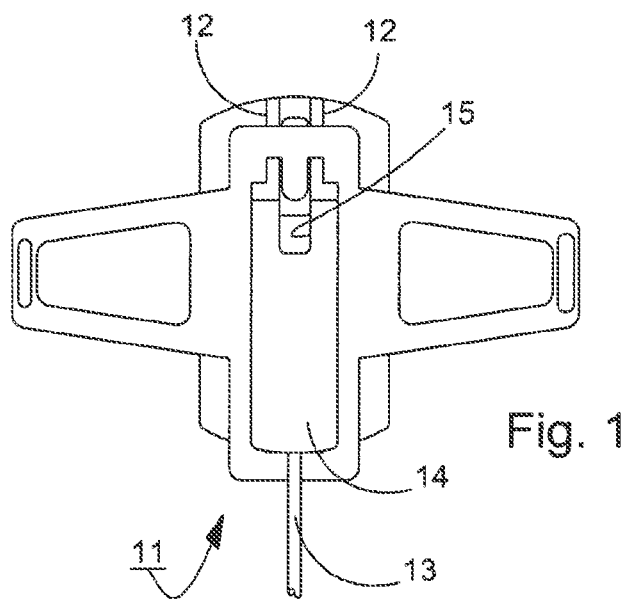
FIG. 1 illustrates a top view of a connector in accordance with the invention mounted on a housing of a Huber needle assembly.

Referring to FIG. 1, the connector 10 is constructed for snap fitting onto the housing 11 of a Huber needle assembly. By way of example, the Huber needle assembly is constructed as described in the above-noted US 2008/0262434.

Figure 2:
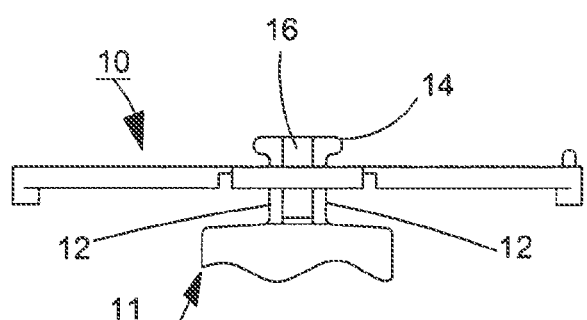
FIG. 2 illustrates an end view of the connector and housing of FIG. 1.

Referring to FIGS. 1 and 2, the housing 11 is provided with a gripping surface formed by a pair of parallel upstanding longitudinally extending walls 12 that define a passage way for a flexible tube 13 that connects to one leg (not shown) of a Huber needle located between the walls 12. In addition, a flange 14 extends laterally across the top of the walls 12 to form an overhang over each wall 12. The flange 14 has a recess 15 at a forward end as shown in FIG. 1.

As indicated in FIG. 2, a transverse wall 16 extends between the longitudinal walls 12 to close off the space between the walls 12 to the outside environment. This transverse wall 16 is located downstream of the depending leg of the Huber needle (not shown) that passes through a port 17 (see FIG. 7) located at a central point in the underside of the housing 11.

Figure 3:
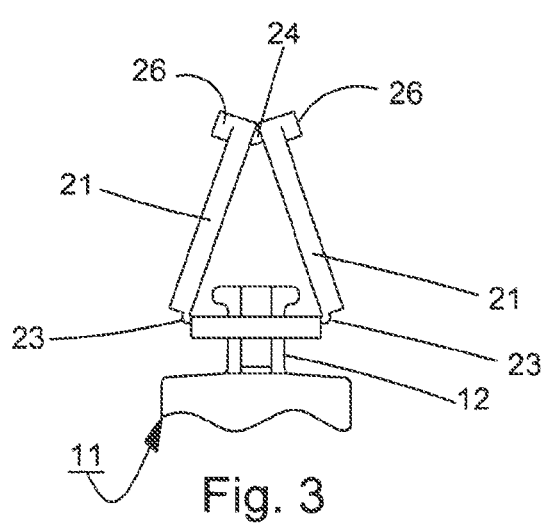
FIG. 3 illustrates an end view similar to FIG. 2 with the wings of the connector pivoted into a position for gripping.
Figure 4:
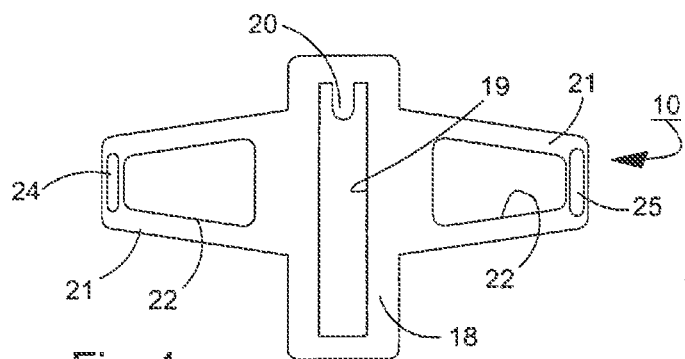
FIG. 4 illustrates a top view of the connector of FIG. 1.

Referring to FIG. 4, the connector 10 is formed of a one-piece body, for example, of semi-rigid polypropylene plastic, to engage the gripping surface of the housing 11. As illustrated, the connector 10 has a flat apertured frame 18 that defines an opening 19 of rectangular shape for fitting about the walls 12 and under the flange 14 of the housing 11 as indicated in FIGS. 1 to 3.

The connector 10 also has a projection 20 that extends from the frame 18 into the opening 19 at a forward end. As indicated in FIG. 1, the projection 20 fits between the walls 12 of the housing 11 in order to stabilize the connector 10 and lock the front end of the connector 10 against any movement relative to the housing 11.

Figure 5:
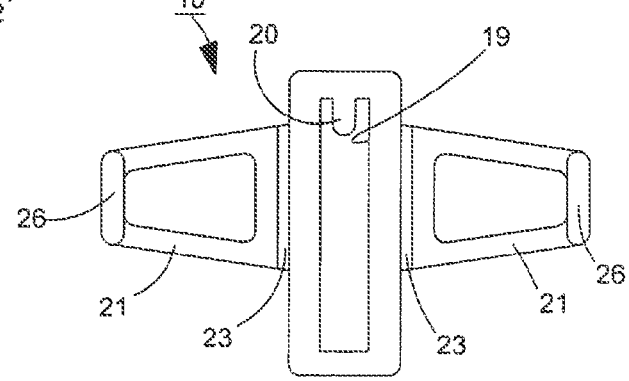
FIG. 5 illustrates a bottom view of the connector of FIG. 1.
Figure 6:
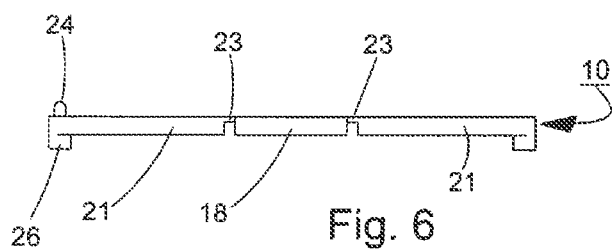
FIG. 6 illustrates an end view of the connector of FIG. 1.

Referring to FIGS. 4, 5 and 6, the connector 10 also has a pair of wings 21 extending from opposite sides of the frame 18. Each wing 21 is of trapezoidal shape with a trapezoidal aperture 22 so as to present a skeletal construction.

As indicated in FIGS. 5 and 6, each wing 21 is hinged to the frame 18 via a hinge 23 of reduced thickness. The hinges 23 allow the wings 21 to be pivoted relative to the frame into a position as indicated in FIG. 3 with the ends of the wings 21 in contact with each other.

Referring to FIGS. 4 and 6, one wing 21 is provided with a projection 24 at the free end thereof while the other wing 21 has a recess 25 at the free end for receiving the projection 24 of the opposite wing 21 (see FIG. 3).

As indicated in FIG. 5, each wing 21 has an outwardly extending rib 26 on the underside of the free end to provide a gripping ledge when the wings 21 are pivoted into contact with each other as shown in FIG. 3.

The design of the wings 21 is such that the wings 21 do not add to the perceived size of the Huber needle assembly since the skeletal-like profile is not very visible.

Further, the wings 21 may be color-coded to indicate needle gauge size. For example, yellow wings would indicate a 20 gauge needle.

Figure 7:
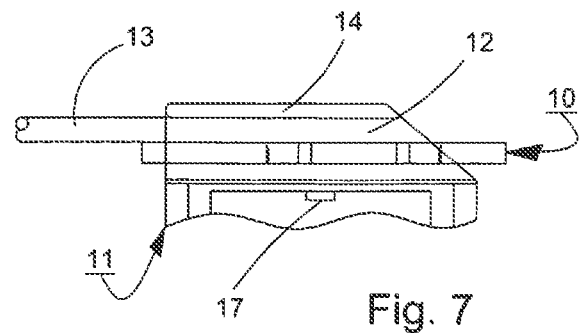
FIG. 7 illustrates a side view of the connector as mounted on the housing of FIG. 1.

When assembling the Huber needle assembly, the connector 10 is snapped over the gripping surface of the housing 11 into a position as shown in FIGS. 1, 2 and 7. At this time, the frame 18 of the connector 10 is located below and under the flange 14 of the housing 11.

When inserting the Huber needle assembly into a patient, the wings 21 of the connector 10 may be pivoted upwardly into the position indicated in FIG. 3. At this time, the user would grip the wings 21 and exert a downward force on the wings 21. This, in turn, would cause the housing 11 and Huber needle therein to move into the patient. After placement of the Huber needle assembly, the wings 21 may be pivoted into a flattened condition against the skin of the patient and taped down using suitable tape strips.

When removing the Huber needle assembly from a patient, the wings 21 are pivoted upwardly into the position indicated in FIG. 3. At this time, the user grips the wings 21 and exerts an upward pulling force on the wings 21 and against the ribs 26. This, in turn, causes the connector 10 to lift thereby pulling the housing 11 and Huber needle therein from the patient.

The advantage of employing the connector 10 resides in the fact that there is no need to manufacture a housing of the Huber Needle assembly with a mechanism for withdrawal of the assembly from a patient. Further, the connector can be maintained in a sterile sealed condition in a suitable package until ready for use on a Huber needle assembly.

The connector 10 is advantageously molded from a soft material, such as polypropylene, that is comfortable to the touch. The wings 21 of the connector 10 are very flexible thereby allowing the connector 10 to be easier to handle than existing rigid housings.

Further, the wings 21 of the connector 10 provide an enlarged surface area for gripping by the fingers of a user as opposed to the user gripping only the gripping surface provided by the upstanding walls 12 of the housing 11.

What is claimed is:

1. A device for removing a Huber needle from a patient, comprising:
    a housing mounted on the Huber needle, including:
        a first wall adjacent a first side of the needle;
        a second wall adjacent a second side of the needle opposite the first side; and
        a flange extending laterally across the top of the first wall and the second wall to form an overhang thereover; and
    a connector having a flat apertured frame disposed on the housing, including:
        an opening having a first side adjacent the first wall and a second side adjacent the second wall, the first and second sides engaging the flange as the needle is removed from the patient; and
        a first wing adjacent the opening first side and a second wing adjacent the opening second side, the first and second wings hinged to the frame to permit pivoting toward one another.

2. The device according to claim 1, wherein the connector further includes a projection extending into the opening between the first and second sides.

3. The device according to claim 2, wherein the flange includes a recess at an end thereof, the recess receiving the projection.

4. The device according to claim 1, wherein the connector is a one-piece body of plastic.

5. The device according to claim 4, wherein the plastic is a semi-rigid polypropylene.

6. The device according to claim 1, wherein the first and second wings have a trapezoidal shape, and each includes a trapezoidal-shaped aperture.

7. The device according to claim 1, wherein the first wing includes a recess at an end thereof and the second wing includes a projection at an end thereof that is received by the recess of the first wing when the first and second wings are pivoted into contact with one another.

8. The device according to claim 1, wherein each of the first and second wings includes an outwardly extending rib on an underside of a free end thereof to provide a gripping ledge when the first and second wings are pivoted into contact with one another.

* * * * *